US008240472B2

United States Patent
Khan

(10) Patent No.: US 8,240,472 B2
(45) Date of Patent: Aug. 14, 2012

(54) COMBINATION BANDAGE AND WOUND TREATMENT SYSTEM

(76) Inventor: Sitara R. Khan, Old Westbury, NY (US)

( * ) Notice: Subject to any disclaimer, the term of this patent is extended or adjusted under 35 U.S.C. 154(b) by 0 days.

(21) Appl. No.: 12/734,105

(22) PCT Filed: Nov. 10, 2008

(86) PCT No.: PCT/US2008/083057
§ 371 (c)(1),
(2), (4) Date: Jun. 28, 2010

(87) PCT Pub. No.: WO2009/062191
PCT Pub. Date: May 14, 2009

(65) Prior Publication Data
US 2010/0270203 A1    Oct. 28, 2010

Related U.S. Application Data

(60) Provisional application No. 60/986,742, filed on Nov. 9, 2007.

(51) Int. Cl.
*A61L 15/00* (2006.01)
(52) U.S. Cl. ........................ 206/440; 206/441
(58) Field of Classification Search .................. 206/440, 206/441, 210, 812, 361
See application file for complete search history.

(56) References Cited

U.S. PATENT DOCUMENTS

| | | | | |
|---|---|---|---|---|
| 4,427,111 A * | 1/1984 | Laipply | ........................ | 206/210 |
| 4,674,634 A * | 6/1987 | Wilson | ........................ | 206/554 |
| 4,796,751 A * | 1/1989 | Madkour | ........................ | 206/223 |
| 5,111,934 A * | 5/1992 | Morin | ........................ | 206/229 |
| 5,487,932 A * | 1/1996 | Dunshee | ........................ | 428/68 |
| 5,511,689 A * | 4/1996 | Frank | ........................ | 221/73 |
| 5,562,642 A * | 10/1996 | Smith et al. | ........................ | 604/289 |
| 5,771,524 A * | 6/1998 | Woods et al. | ........................ | 15/209.1 |
| 6,007,264 A * | 12/1999 | Koptis | ........................ | 401/132 |
| 6,446,795 B1 * | 9/2002 | Allen et al. | ........................ | 206/210 |
| 6,923,320 B2 * | 8/2005 | Grossman | ........................ | 206/440 |
| 6,967,261 B1 * | 11/2005 | Soerens et al. | ........................ | 602/48 |
| 7,240,790 B2 * | 7/2007 | Wendel et al. | ........................ | 206/210 |
| 7,661,552 B2 * | 2/2010 | Baum et al. | ........................ | 221/41 |
| 2006/0155251 A1 * | 7/2006 | Assie et al. | ........................ | 604/306 |
| 2006/0163101 A1 * | 7/2006 | Assie et al. | ........................ | 206/440 |
| 2009/0216169 A1 * | 8/2009 | Hansen et al. | ........................ | 602/48 |

* cited by examiner

*Primary Examiner* — David Fidei
(74) *Attorney, Agent, or Firm* — Thomas A. O'Rourke; Bodner & O'Rourke, LLP

(57) ABSTRACT

A wound treatment system including a housing having a first compartment and a second compartment, a bandage disposed within the first compartment, and a swab disposed within the second compartment. Further, the first compartment is openable independent of the second compartment, and the second compartment is openable independent of the first compartment. The wound treatment combination and bandages provides access to both disinfecting along with treating topically as well as covering wounds and scars at nearly sterile conditions to allow optimal healing and lowering the risk of infection and contamination and scars. The variable sizes envisioned allows for treatment of both small as well as larger surfaces.

20 Claims, 5 Drawing Sheets

COMBINATION BANDAGE AND WOUND TREATMENT SYSTEM

CROSS-REFERENCE TO PRIOR APPLICATIONS

This application claims priority to U.S. Provisional Application Ser. No. 60/986,742, filed Nov. 9, 2007, entitled "Combination Bandage and Wound Treatment System," the contents of which are incorporated herein by reference in its entirety.

FIELD

The present invention generally relates to wound care, and more particularly relates to bandages and wound treatment swabs and combination medication.

BACKGROUND

Typically, when injuries or disease related wounds occur, the wound should first be cleaned to prevent any infection from occurring at the wound cite. This is usually accomplished by applying an antiseptic, commonly alcohol or iodine. This entails pouring the antiseptic from a bottle and applying it to a swab, usually gauze or a cotton ball, which will be used to wipe the wound clean of dirt and germs. At this point it may be desirable to apply an antibiotic, a pain reducer, an antiviral medication, a scar treatment or the like. Once the wound has been treated, it is necessary to cover the wound site with a bandage in order to prevent external bacteria from infecting the wound and to provide a protected and sterile environment in which the wound may heal.

The current method of wound care would require a person to have with them, especially if that person is traveling, a bottle of antiseptic, a package of swabs, a package of bandages, as well as other desired treatment compositions such as those mentioned above. Thus, many people are discouraged from having available these wound care products, resulting in wounds that are not cared for properly. This improper wound care may lead to more serious health conditions, excessive scarring and pain and numerous trips to the doctor, all of which could have been avoided with timely care. Thus, what is needed is a bandage and wound treatment which can be provided together which would be relatively compact, light and easy to carry, but nevertheless provide all that is necessary to properly care for different types of wounds.

SUMMARY

The present invention generally relates to wound care, and more particularly relates to bandages and wound treatment swabs.

An embodiment of the present invention provides a wound treatment system. The wound treatment system includes a housing having a first compartment and a second compartment, a bandage disposed within the first compartment, and a swab disposed within the second compartment. Further, the first compartment is openable independent of the second compartment, and the second compartment is openable independent of the first compartment

BRIEF DESCRIPTION OF THE DRAWINGS

The present invention will be more readily understood from the detailed description of exemplary embodiments presented below considered in conjunction with the accompanying drawings, in which.

DETAILED DESCRIPTION

Figure 1:
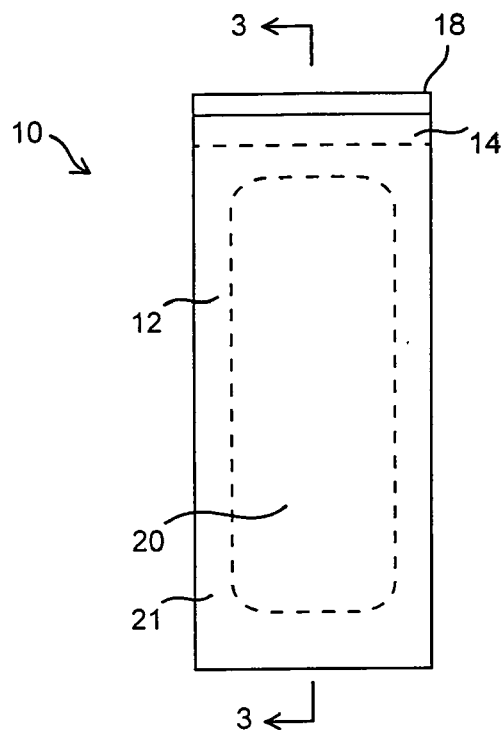
FIG. 1 is a front view showing a bandage and wound treatment swab combination according to one embodiment of the invention.
Figure 2:
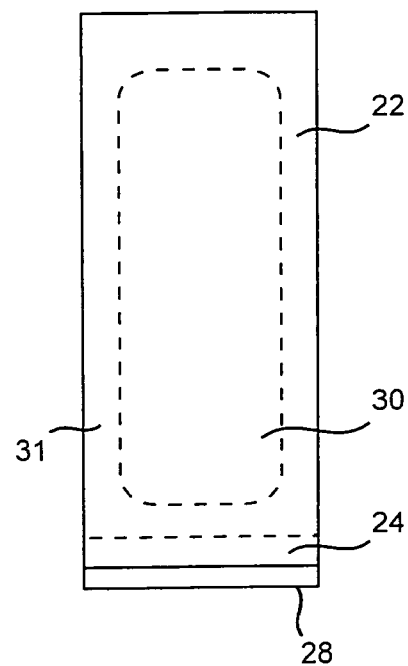
FIG. 2 is a rear view thereof.

Referring now to FIGS. 1-4, the combination bandage and wound treatment article 10 includes a bandage 40 provided together with and a wound treatment swab 42. Both the bandage 40 and the swab 42 are each packaged within separate compartments of the combination bandage and wound treatment article 10.

The bandage 40 is disposed between a first package strip 12 and the second package strip 18. The perimeters of the first and second package strips 12 and 18 are bonded together. The strips can be bonded together with adhesive, by heat melting, by acoustic fusing, or other means. The center portions of the strips 12 and 18 are not bonded together, thus forming a pouch 20. The pouch 20 provides a sealed compartment for the storage of the bandage 40. Thus, disposing a bandage 40 between the strips 12 and 18 and then bonding the outer perimeters of the strips together seals the bandage 40 between the two strips 12 and 18. This provides a sterile and protective storage compartment for the bandage 40. Accordingly, the bandage 40 can be safely and cleanly stored between the strips 12 and 18 in the pouch 20 until the bandage is needed.

The bandage 40 can be various types of wound dressing, but is preferably an adhesive type bandage having an absorbent portion and adhesive surfaces for holding the bandage against the skin of a wounded user. The bandage 40 can be of various sizes and shapes and can be made of any appropriate material or its combination. Its size can vary from a few centimeters to as large as a dozen or more inches. Further, the bandage can be treated with various substances such as antibiotics, scar reducers, and other substances which can promote the healing of the wound. The bandage can be waterproof or breathable. The bandage can have a fabric strip. The absorbent portion can be a cotton pad or other suitable material, and may be designed so that is does not stick to the wound when the bandage is removed and may include a protective sheathing over the absorbent portion. The absorbent portion of the bandage may also assist with the treatment of wounds that involve envenomation of the user. The absorbent portion can be capable of absorbing at least a portion of the venom at or near the surface of the wound. The bandage (and/or wound treatment swab) can be treated with a topical absorbed anti-venom substance such that applying the bandage to the wound would result in administration of the anti-venom. The absorbent portion can also absorb contaminants.

Further, the bandage can be such that it holds the wound together, applying tension when applying the bandage will pull the skin surfaces surrounding an open wound together, which can act as a kind of adhesive skin closure such as those commonly available under the trade name Steri-Strip™ (material used instead of a suture that sticks tight to the surfaces of skin and is sometimes used to close lacerations). The bandage 40 may also be an adhesive strip, in which case the wound treatment swab 42 can be placed on the wound and the adhesive strip can be used to hold the swab 42 in place against the wound. This arrangement can have a broader application than a bandage and could have medical applications in treating facilities, operating rooms, etc.

The first and second strips 12 and 18 can be made of various materials. The strips 12 and 18 can be for example wax coated paper, plastic, foil or other suitable material. The strips are designed to provide protection for the bandage 40 and the help maintain the bandage 40 in a sterile condition. Further, if the bandage 40 is treated with a particular substance, such as an antibiotic, the strips will help maintain the integrity of the antibiotic substances and can help prevent it from drying out or evaporating or otherwise prevent loss of the substance. The bandage can contain dry, powder, or moist compositions and the compositions can be, for example, antibiotic, antiviral, antifungal, burn treatment (e.g. cream), a wound healing stimulator (e.g. chemical, growth-healing factor stimulators), scar remover/reducer, wound shrinker, pain reliever, itch reliever, etc.

The wound treatment swab 42 is disposed between a third package strip 22 and a fourth package strip 28. The perimeters of the third and fourth package strips 22 and 28 are bonded together. The strips can be bonded together with adhesive, by heat melting, by acoustic fusing, or other means. The center portions of the strips 22 and 28 are not bonded together, thus forming a pouch 30. The pouch 30 provides a sealed compartment for the storage of the wound treatment swab 42. Thus, disposing a wound treatment swab 42 between the strips 22 and 28 and then bonding the outer perimeters of the strips together seals the wound treatment swab 42 between the two strips 22 and 28. This provides a sterile and protective storage compartment for the wound treatment swab 42. Accordingly, the wound treatment swab 42 can be safely and cleanly stored between the strips 22 and 28 in the pouch 30 until the wound treatment swab is needed.

The wound treatment swab 42 can be various types of treatment swabs. The wound treatment swab can be an alcohol swab, an iodine solution swab, and antibacterial/antibiotic wipe or other swab, wipe, or towelette for treating and/or cleaning a wound and the surrounding area. The swab may be a gauze pad, ribbon, strip, roll, ball (e.g. cotton ball) for example. The wound treatment swab can be treated with a cream or composition for treating burns, can contain anti-allergens, anti-virals, antifungal, anti-inflammatory compositions, scar treatments, wound/scar hydrating solution, vitamins, or any other suitable material/compound or any combination thereof. The swab may have purified water for cleaning the wound, lidocaine for pain, and betadine for antiseptic/antibacterial treatment, for example. A wound cleanser solution may for example be an antibacterial like betadine. In addition, the treatment material may be an antibiotic, etc. to address the wound and may also include antiviral medication and a pain reducer (e.g. lidocaine/topical anestetic) which, for example with a user with a viral infection such as shingles, can provide a sterile (e.g. with the inclusion of the antibiotics) all in one treatment.

The third and fourth strips 22 and 28 can be made of various materials. The strips 22 and 28 can be for example plastic, foil, foil coated paper or other suitable material. The strips are designed for provide protection for the wound treatment swab 42 and the help maintain the wound treatment swab 42 in a sterile condition. Further, the strips will help maintain the integrity of the alcohol, iodine solution, antibacterial or other solutions of the swab and can help prevent the swabs from drying out and the wound treatment solutions from evaporating.

Figure 3:
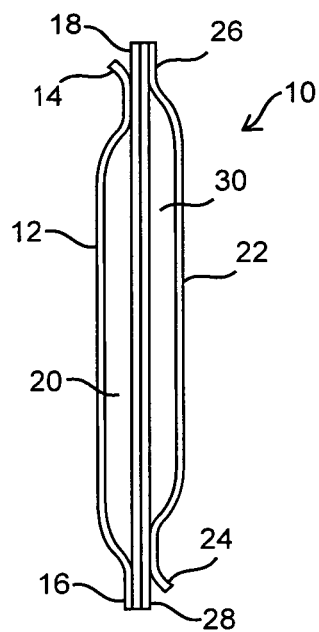
FIG. 3 is a cross-sectional view thereof along line 3-3 of FIG. 2.
Figure 4:
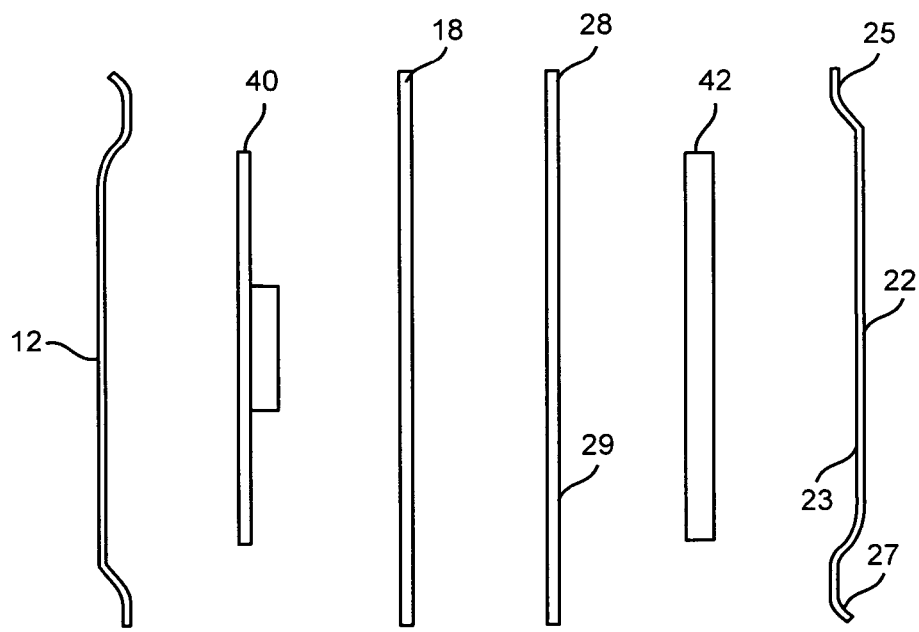
FIG. 4 is a side exploded view thereof

The second strip 18 and the fourth strip 28 are bonded together, as more clearly shown in FIGS. 3 and 4. Thus, the combination bandage and wound treatment article 10 can provide both a bandage 40 and a wound treatment swab 42 in separate pouches 20 and 30, respectively, in a single article 10. Strips 18 and 28 act as a barrier to keep the bandage 40 and the treatment swab 42 separate from each other. Accordingly, when a wound needs to be treated and dressed, a-user can use the combination article 10 to provide all the materials necessary to treat and dress the wound in a single convenient article. Thus, a user will not have to find a separate wound treatment article, such as an alcohol swab in order to treat the wound, and a separate bandage to dress the wound. Both the swab and bandage are provided together in a single article 10.

Further, by providing both the treatment swab and the bandage together, proper wound care techniques can be promoted. Many times a user that has experienced a wound may only seek a bandage to dress the wound and help stop bleeding. However, the user may use the bandage without properly cleaning or treating the wound. This may be because the user may not have wound treatment swabs (e.g. alcohol swabs) readily available either because they are not stored with the bandages, the user never purchased swabs and therefore are not available, or the additional steps of getting a treatment swab may be avoided by the user.

By providing a treatment swab together with a bandage, the wound treatment swab is always readily available when the user seeks to use a bandage. This increases the likelihood that a user will use the wound treatment swab before dressing the wound with the bandage. Thus, the article 10, which provides a bandage 40 and a wound treatment swab 42 together, will help promote proper wound treatment. Further, the article 10 is designed to be a one-time use disposable article. Once the user uses the bandage/wound treatment swab, the article 10 can be discarded. This will additionally increase the likelihood that a user will use the wound treatment swab before dressing the wound with the bandage. If the user only used the bandage and not the wound treatment swab, the user will be faced with the prospect of discarding the article 10 containing an unused swab 42. The user may feel uncomfortable and wish to avoid throwing away and "wasting" an unused swab 42, and therefore the user may be inclined to use the swab so that it is not wasted. Alternately, the separate packaging of the bandage and swab allows the user to use one or the other without opening the pouch of the other.

The strips of the article 10 are bonded together such that the pouches can be opened easily and at separate times from each other. As shown in FIG. 3, end 16 of first strip 12 is completely bonded to second strip 18. The opposite end of first strip 12 is not completely bonded to second strip 18. The free end portion of the first strip 12 that is not bonded to the second strip 18 forms a tab 14 that is not bonded to the second strip 18: The tab 14 can be used to peel first strip 12 away from second strip 18 to open pouch 20 and provide access to the bandage 40 stored therein. By gripping tab 14 and the proximate end of second strip 18, fourth strip 28, and end 26 of third strip 22 and pulling tab 14 in an opposite direction from the proximate end of second strip 18, fourth strip 28, and end 26 of third strip 22, the first strip 12 can be peeled away from second strip 18 to open pouch 20.

First strip 12 may be bonded with an adhesive that is strong enough to maintain first strip 12 bonded to second strip 18 during handling, but can be overcome by a user attempting to open pouch 20 by pulling away first strip 12. In addition, first strip 12 can be shorter than second strip 18 so that the tab 14 and the proximate end of the second strip 18 can be more easily gripped to facilitate opening of the pouch 20.

The third strip 22 is bonded to fourth strip 28 in a similar way as the first and second strips 12 and 18, thus forming tab 26. However, tab 26 is located on an end opposite tab 14. Thus, by gripping and pulling the strips at one end of the article 10, one pouch may first be opened, and then by gripping and pulling the strips at the opposite end of the article 10, the second pouch may be opened. This arrangement facilitates separate opening of the pouches so that accidental opening of the pouches does not occur. Thus, a user can open pouch 30 containing wound treatment swab 42 to treat the wound first, while maintaining the bandage 40 sealed and protected in pouch 20 until it is ready to be used. After the wound has been treated with the treatment swab 42, pouch 20 can be opened to gain access to the bandage 40 to dress the wound. Alternatively, the strips and the packaging can be arranged so that tab 14 and tab 26 are located at the same end of the package.

Alternatively, the strips can be attached such that the tabs are located along the sides of the package. Thus, the pouches can be opened from the side.

Figure 5:
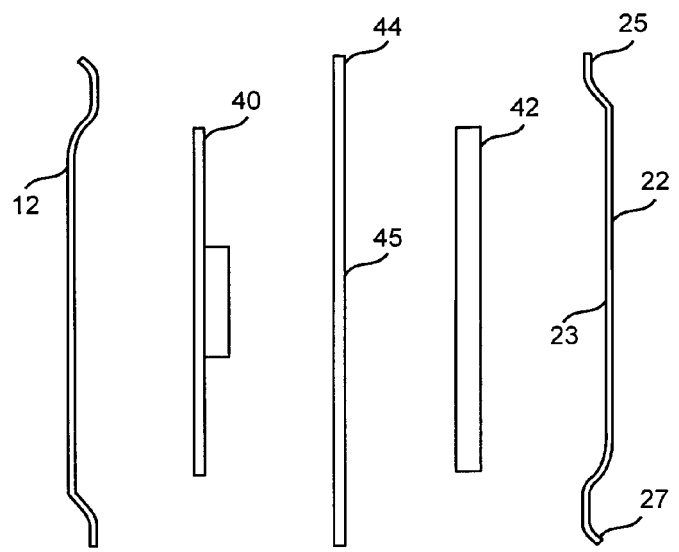
FIG. 5 is a side exploded view of a further embodiment.

In addition, the wound treatment swab 42 can be attached to strip 22 or 28 (or 22 or 44 when an arrangement such as that shown in FIG. 5 is provided) by, for example, adhesive. Thus, when strips 22 and 28 are pulled apart to open pouch 30, the swab 42 remains attached to strip 22 or 28. Therefore, the user can hold either strip 22 or the rest of the packing to which strip 28 may be attached, to treat (e.g. wipe, clean, disinfect) the wound with the surfaces of the swab 42 that are not attached to the strip with out directly contacting swab 42 and potentially contaminating the swab or soiling the hand of the user.

Figure 8:
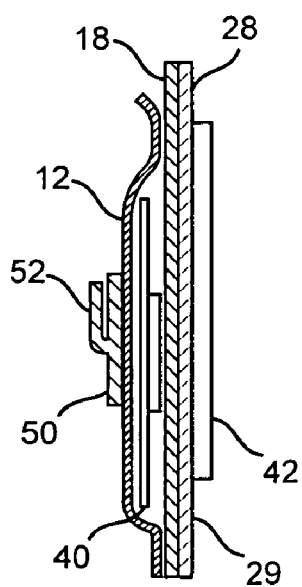
FIG. 8 is a side view showing a bandage and wound treatment swab combination according to another further embodiment of the invention.
Figure 9:
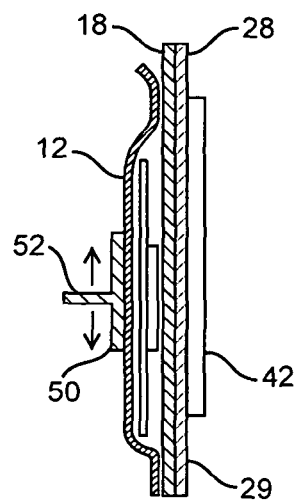
FIG. 9 is a side view thereof in another state.
Figure 10:
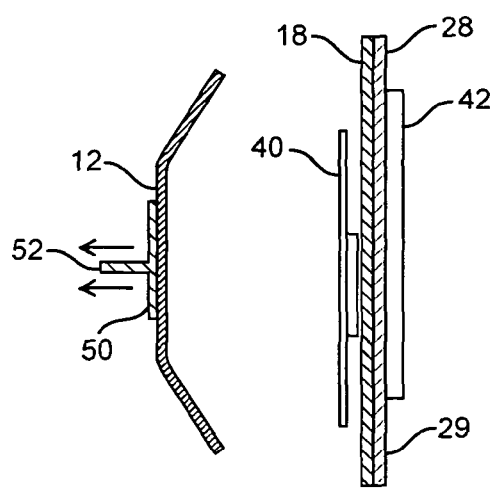
FIG. 10 is a side view thereof in still another state.
Figure 11:
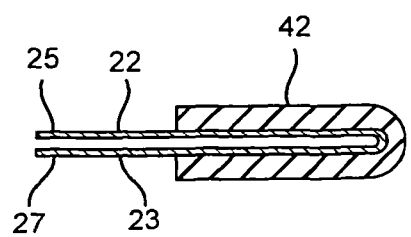
FIG. 11 is a side view showing a swab attached to a strip.

As shown in FIG. 8, for example, the swab 42 is attached to surface 29 of strip 28 and strip 22 has been removed to open pouch 30 and expose swab 42. The swab 42 could also be attached to surface 45 of strip 44 when arrangement such as that shown in FIG. 5 is provided. A gripping tab 50 is attached to strip 12, which can assist in using swab 42 to treat a wound without touching swab 42. The gripping tab 50 can be made out of the same material as strip 12 or can be any other suitable material. The gripping tab 50 can also be formed by creating a fold in the strip 12. The gripping tab 50 includes a handle portion 52, which can be initially kept in the folded down position as shown in FIG. 8 with a releasable adhesive, by a fold, or any other suitable means. When the user wants to treat a wound with swab 42, the handle 52 can be rotated into an extended position as shown in FIG. 9. Thus, the user can grip the handle portion 52 and use it to grip and move the article (e.g. in a direction indicated by the arrows) over the wound. Further, as shown in FIG. 10, a user can grip handle 52 and pull (e.g. in a direction indicated by the arrows) to open pouch 20 be separating strip 12 from strip 18 to gain access to the bandage 40. Alternatively, when the swab is attached to surface 23 of strip 22, a gripping tab 50 can be attached to the opposite surface of strip 22. As another means of treating a wound without contacting the swab 42, when the swab 42 is attached to strip 22, strip 22 can be folder over as shown in FIG. 11. Then, the user can grip ends 25 and 27 of strip 22 and treat the wound with swab 42.

As shown in FIG. 4, article 10 includes two strips, strips 18 and 28, which act as a barrier between the bandage 40 and the swab 42. In this way, the bandage 40 can be packaged separately from swab 42. Bandage 40 can be packaged between strips 12 and 18 at one location and swab 42 can be packaged between strips 22 and 28 at another location, and then strips 18 and 28 can be bonded together to form article 10. However, a single barrier strip 44 may be used instead of strips 18 and 28, as shown in FIG. 5. Thus, bandage 40 can be packaged between strip 12 and barrier strip 44, which are bonded together, and swab 42 can be packaged between strip 22 and barrier strip 44, which are also bonded together.

Figure 6:
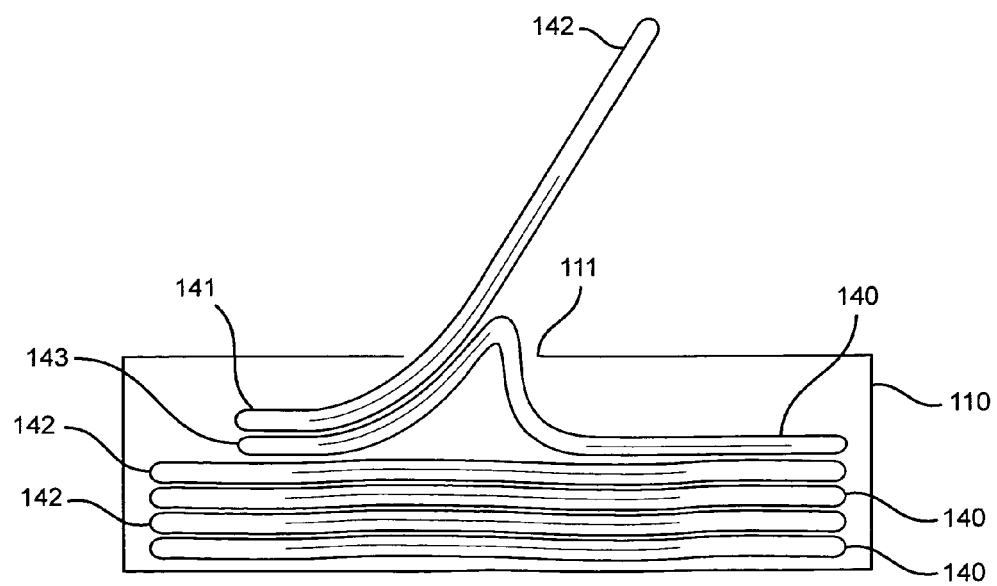
FIG. 6 is a side view of a bandage and wound treatment swab combination and dispenser.
Figure 7:
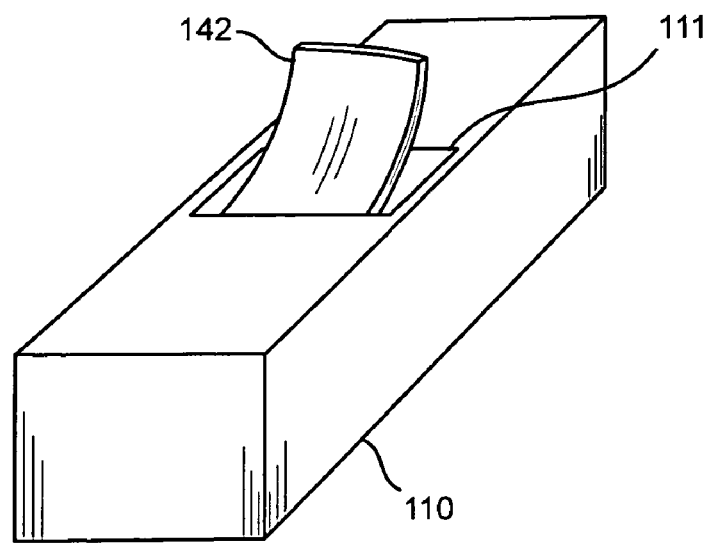
FIG. 7 is an isometric view thereof.

Individually packaged bandages and wound treatment swabs may be provided together as shown in FIGS. 6 and 7. The bandages 140 and wound treatment swabs 142 are separately packaged in sterile and protective packaging. The separate packages are stored in a dispenser 110 in an alternating interleaved fashion. Thus, the bandages 141 and wound treatment swabs 142 are stacked in the dispenser 110 in the order of swab, bandage, swab, bandage and continues to repeat in that order. Thus, when the dispenser pack is freshly loaded, a swab is presented first for dispensing. When a user looking to treat the wound uses the dispenser, a swab is first readily available for dispensing for cleaning/treating the wound. After the swab has been removed from the dispenser, a bandage is next ready to be dispensed. Thus, after the wound has been treated, a bandage is ready to be dispensed so that the wound may be dressed. After the bandage has been removed from the dispenser, a swab is next ready to be dispensed which can be used for treating the next wound. The serial dispensing of alternating swabs and bandages can help in the fast and efficient care of wounds.

As shown in FIG. 6, one end 141 of the first package is releasably adhered to an end 143 of the next package to be dispensed. Thus, as the first package is removed through dispenser slot 111, the next package is pulled through the dispenser slot 111 and presented for dispensing. The adhesive between the first and next package is strong enough to ensure that the next package is pulled through the slot and presented for dispensing, but easily releases from the first package so that it may be removed without fully removing the next package from the dispenser.

The individually packaged bandages 141 and wound treatment swabs 142, may be replaced inside the dispenser 110 with combination packaged bandages and wound treatment swabs, such as the combination bandage and wound treatment article 10 described above.

The dispenser 110 is suitable for table top dispensing or may include a clip so that is can be worn on the belt of a user. Thus, the dispenser can be readily accessible to person responding to wound treatment in mobile situations. For example, the dispenser can be worn on the belt of a hiker. The dispenser may also include a cover to seal and protect its contents, which can also provide a waterproof seal.

In one embodiment, the wound treatment swab 42 is a gauze pad. The gauze pad can be folded or rolled so that it may be packaged in a small pouch area, and then unfolded to a larger size when removed from the package. The user can then cut off a piece of the unfolded gauze pad sheet to apply to a wound. The sheet could also be perforated so that pre-sized portions of the sheet can be separated. The sheet can be large enough so that several pieces can be cut to treat several wound sites. The gauze pad can be treated with various different compositions or any combination thereof for the treatment of various wounds or ailments. For example, the pad can be treated with an antiviral (e.g. aciclovir cream which may also be known under brand name Zorvirax™), pain reliever (e.g. lidocaine), and an antibiotic in combination to treat shingles. As another example, the pad can be treated with an antibiotic burn cream (e.g. Silver Sulfadiazine, which may also be known under brand name Silvadene) and a pain reliever (e.g. lidocaine) in combination to treat burns. As a further example which would be useful for treating abrasions, the pad can be treated with an antibiotic (or triple combination of antibiotics) and a pain reliever (e.g. lidocaine) in combination. As another further example which would be useful for treating rashes, the pad can be treated with an antibiotic (or triple combination of antibiotics), a steroid, and an antifungal composition in combination. Other compositions can be used also, such as human growth factor, wound healing factor, vitamins (for example vitamin E or other vitamins which would promote wound healing), topical scar treatments (e.g. Mederma®), and combinations thereof. Thus, the cut pieces of the pad can be applied to the wound. The treated gauze pad can be packaged alone, or can be provided in a combination package with a separate pouch containing an adhesive tape which can be used to hold the gauze pad in place over the wound. Further, the above described treatment compositions and other combinations can be packaged alone or in a combination package wherein a treatment composition in the form of a cream or liquid for example, is contained in one pouch and a dressing is contained in a separate pouch. Thus, the cream can be obtained by opening the first pouch, which can then be applied to the wound, and then dressing can be obtained from the second pouch and used to dress the wound.

While the invention has been particularly shown and described with reference to preferred embodiments thereof, it will be understood by those skilled in the art that various changes in form and details may be made therein without departing from the spirit and scope of the invention.

I claim:

1. A wound treatment system, comprising: a housing having a first compartment and a second compartment; said housing comprising a first outer sheet and a second outer sheet, each of said outer sheets of said housing having an inner surface and an outer surface, said inner surface of said first outer sheet contacting a first surface of a strip positioned between said inner surfaces of said outer sheets of said housing and forming said first compartment, said strip being removably secured to said inner surface of said first outer sheet, said inner surface of said second outer sheet contacting a second surface of a strip positioned between said inner surfaces of said outer sheets of said housing and forming said second compartment, said strip being removably secured to said inner surface of said second outer sheet, a bandage removably disposed within the first compartment; said second outer sheet having a swab disposed on an inner surface of said second outer sheet within the second compartment, wherein the first compartment is openable independent of the second compartment, and the second compartment is openable independent of the first compartment and wherein said swab covers only a portion of said second sheet and wherein there is a swab free portion at opposite ends of said second sheet and wherein said second sheet when separated from said strip is foldable so that said swab free portion of said second sheet may be gripped without contacting said swab when said sheet is folded.

2. The wound treatment system as recited in claim 1, wherein the housing includes a plurality of package strips, and wherein each compartment is an interior formed between a first and a second package strip coupled to each other along a perimeter of the first and second package strips.

3. The wound treatment system as recited in claim 2, wherein the first and second compartments share a common package strip.

4. The wound treatment system as recited in claim 2, wherein the swab is attached to one of the plurality of package strips.

5. The wound treatment system as recited in claim 2, further comprising at least one gripping tab attached to one of the plurality of package strips.

6. The wound treatment system as recited in claim 5, wherein the at least one gripping tab is configured to allow a user to handle the swab.

7. The wound treatment system as recited in claim 1, wherein the bandage includes a treatment, the treatment including at least one of an antibiotic, a scar reducer, an antiviral, a burn cream, a wound healing stimulator, a pain reliever, and an itch reliever.

8. The wound treatment system as recited in claim 1, wherein the swab includes a treatment, the treatment including at least one of an alcohol, an antiseptic, an antibacterial, an antibiotic, an anti-inflammatory composition, a scar treatment, a pain reliever, a burn cream, an anti-allergen, a vitamin, and purified water.

9. The wound treatment system as recited in claim 1, wherein at least one of the first compartment and the second compartment is sterile.

10. The wound treatment system as recited in claim 1, further comprising a dispenser configured to dispense the bandage disposed within the first compartment and the swab disposed within the second compartment.

11. The wound treatment system as recited in claim 10, wherein at least one of the bandage and the swab are interleaved disposed within the dispenser.

12. The wound treatment system as recited in claim 10, wherein the dispenser is configured so that in dispensing at least one of the bandage and the swab, an adjacent bandage or swab is at least partially dispensed from the dispenser.

13. A wound treatment device comprising: a first packing strip, a second packing strip, and a third packing strip; a first compartment formed between the first packing strip and the second packing strip; a second compartment formed between the second packing strip and the third packing strip; a bandage disposed within the first compartment; a swab attached to the third packing strip, the first packing strip being coupled to a first surface of the second packing strip along a perimeter of the first and second packing strips in forming the first compartment, the third packing strip being coupled to a second surface of the second packing strip along a perimeter of the third and second packing strips in forming the second compartment, wherein the first compartment is openable independent of the second compartment and the second compartment is openable independent of the first compartment, and wherein the swab on said third packing strip has a first wound contact surface and a second surface opposite the wound contact surface said second surface being directly attached to the inner surface of the third packing strip and wherein said swab covers only a portion of said third packing strip and wherein there is a swab free portion at opposite ends of said third packing strip and wherein said third strip is foldable so that said swab free portion of said third packing strip may be gripped without contacting said swab when said third packing strip is folded.

14. The wound treatment device as recited in claim 13, further comprising at least one gripping tab configured to allow a user to handle the swab.

15. The wound treatment device as recited in claim 13, wherein the bandage includes a treatment, the treatment including at least one of an antibiotic, a scar reducer, an antiviral, a burn cream, a wound healing stimulator, a pain reliever, and an itch reliever.

16. The wound treatment device as recited in claim 13, wherein the swab includes a treatment, the treatment including at least one of an alcohol, an antiseptic, an antibacterial, an antibiotic, an anti-inflammatory composition, a scar treatment, a pain reliever, a burn cream, an anti-allergen, a vitamin, and purified water.

17. The wound treatment system according to claim 1 wherein when said second sheet is folded a portion of said swab is on both sides of said folded second sheet.

18. The wound treatment system according to claim 17 wherein said second sheet has a first end and a second end and wherein when said second sheet is folded and gripped by a user one surface of said first end contacts a surface of the opposite end of said second sheet.

19. The wound treatment device according to claim 13 wherein when said third strip is folded a portion of said swab is on both sides of said folded third strip.

20. The wound treatment device according to claim 19 wherein said third strip has a first end and a second end and wherein when said third strip is folded and gripped by a user one surface of said first end contacts a surface of the opposite end of said third strip.

* * * * *